United States Patent
Mori (10) Patent No.: US 11,125,765 B2
(45) Date of Patent: Sep. 21, 2021

(54) AUTOMATIC ANALYZER

(71) Applicant: HITACHI HIGH-TECHNOLOGIES CORPORATION, Tokyo (JP)

(72) Inventor: Hiroki Mori, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 272 days.

(21) Appl. No.: 16/330,426

(22) PCT Filed: Sep. 14, 2017

(86) PCT No.: PCT/JP2017/033326
§ 371 (c)(1),
(2) Date: Mar. 5, 2019

(87) PCT Pub. No.: WO2018/056175
PCT Pub. Date: Mar. 29, 2018

(65) Prior Publication Data
US 2020/0400699 A1  Dec. 24, 2020

(30) Foreign Application Priority Data

Sep. 21, 2016 (JP) .............................. JP2016-183809

(51) Int. Cl.
*G01N 35/00* (2006.01)
*G01N 33/49* (2006.01)
*G01N 33/493* (2006.01)

(52) U.S. Cl.
CPC . *G01N 35/00663* (2013.01); *G01N 35/00693* (2013.01); *G01N 33/49* (2013.01);
(Continued)

(58) Field of Classification Search
CPC ....... G01N 35/00663; G01N 35/00693; G01N 33/49; G01N 33/493; G01N 2035/00673; G01N 2035/0091
See application file for complete search history.

(56) References Cited

U.S. PATENT DOCUMENTS

2009/0093972 A1* 4/2009 Power .............. G01N 33/48785
702/23
2009/0150186 A1* 6/2009 Cohen ..................... G16H 40/63
705/3
(Continued)

FOREIGN PATENT DOCUMENTS

EP    1 762 850 A2    3/2007
EP    2 913 787 A1    9/2015
(Continued)

OTHER PUBLICATIONS

Extended European Search Report received in corresponding European Application No. 17852952.5 dated May 13, 2020.
(Continued)

*Primary Examiner* — Samuel P Siefke
*Assistant Examiner* — Henry H Nguyen
(74) *Attorney, Agent, or Firm* — Mattingly & Malur, PC (57) ABSTRACT

An automatic analyzer allows identification of the patient specimen for which the specific reagent and the standard solution have been used, and verification of reliability of the analysis results. A plot mark 1-10 is determined depending on whether or not codes and lots as management information of the reagent, standard solution, and accuracy control sample are the same as those used last time. The plot 1-3 represents the start of using the reagent, and 1-4 the reagent use area. The plot 1-5 represents generation of calibration curve data from the standard solution and 1-6 a standard solution use area. The plot 1-7 represents measurement of the accuracy control sample and 1-8 an accuracy control sample use area from a time point of measuring the accuracy control sample as indicated by the plot 1-7 until the next time point. The measurement information 1-14 is the region for displaying the measurement results.

7 Claims, 8 Drawing Sheets

(52) U.S. Cl.
CPC ... *G01N 33/493* (2013.01); *G01N 2035/0091* (2013.01); *G01N 2035/00673* (2013.01)

(56) References Cited

U.S. PATENT DOCUMENTS

| | | | | |
|---|---|---|---|---|
| 2009/0214385 A1* | 8/2009 | Mori | ............... | G01N 35/00663 422/63 |
| 2011/0259129 A1* | 10/2011 | Murata | ........... | G01N 35/00693 73/866.3 |
| 2012/0000268 A1 | 1/2012 | Li et al. | | |
| 2013/0266484 A1* | 10/2013 | Kamihara | ........ | G01N 35/00613 422/82.09 |

FOREIGN PATENT DOCUMENTS

| | | | |
|---|---|---|---|
| JP | 2007-248090 | A | 9/2007 |
| JP | 2008-058129 | A | 3/2008 |
| JP | 2009-281802 | A | 12/2009 |
| WO | 2008/050397 | A1 | 5/2008 |
| WO | 2010/073479 | A1 | 7/2010 |
| WO | 2016/140017 | A1 | 9/2016 |

OTHER PUBLICATIONS

International Preliminary Report on Patentability received in corresponding International Application No. PCT/JP2017/033326 dated Apr. 4, 2019.

International Search Report of PCT/JP2017/033326 dated Nov. 21, 2017.

* cited by examiner

| | | |
|---|---|---|
| 3-1 — EXTRACTION OBJECT | ◉ REAGENT  ○ STANDARD SOLUTION  ○ ACCURACY CONTROL SAMPLE | |
| 3-2 — CODE | [          ] | |
| 3-3 — LOT | [          ] | |
| | EXECUTE (3-4) | CANCEL (3-5) |

FIG. 4

PATIENT SPECIMEN 4-1 — EXTRACTION OBJECT : REAGENT   CODE=101901   LOT=000810

4-2

| No. | ID | DATE OF MEASUREMENT | MEASUREMENT RESULT |
|---|---|---|---|
| 1 | 1010534 | 2015/12/01  10:20 | 25.8 |
| 2 | 1001289 | 2015/12/01  10:25 | 32.2 |
| 3 | 1210008 | 2015/12/01  10:28 | 19.8 |
| 4 | 1005411 | 2015/12/01  10:35 | 20.5 |
| 5 | 2001011 | 2015/12/01  10:39 | 23.1 |

4-3

4-4 — CLOSE

FIG. 5

SEARCH 5-1 — PATIENT ID    [           ]

5-2 — EXECUTE    5-3 — CANCEL

AUTOMATIC ANALYZER

TECHNICAL FIELD

The present invention relates to an automatic analyzer configured to execute qualitative/quantitative analysis of a sample such as blood and urine.

BACKGROUND ART

The automatic analyzer is configured to analyze components of a biological sample such as blood and urine using the reagent. Upon start of the analytical process, or in the analytical process in need, the standard solution having a predetermined density is analyzed with respect to each analysis item, and calibration curve data are calculated. Measurement results of the patient specimen are calculated from the calibration curve data.

In the case of the failure in the measurement results of the patient specimen through the use of the automatic analyzer, the cause of the failure has to be found out so as to take a necessary action to solve the problem.

The technology disclosed in Patent Literature 1 is configured to cope with the data failure by starting a condition setting window, selecting the search item, and displaying the search result on another screen so that the patient ID, the classification, the analysis item, the measurement result, and the alarm are displayed.

The technology disclosed in Patent Literature 1 then works to execute the appropriate process such as the cleaning program based on the contents displayed on the search result screen.

CITATION LIST

Patent Literature

Patent Literature 1: Japanese Unexamined Patent Application Publication No. 2009-281802

SUMMARY OF INVENTION

Technical Problem

In operation of the automatic analyzer, if the failure in the reagent or the standard solution is found out to be attributable to the adverse affection on the measurement results of the patient specimen, the use of the concerned reagent or the concerned standard solution is stopped. If the concerned reagent or the concerned standard solution has been already used for analyzing the patient specimen, the corresponding patient specimen has to be identified as soon as possible because of possible diagnostic errors, and then reliability of the analysis results has to be confirmed and verified.

In implementation of the technology disclosed in Patent Literature 1, if there is a possibility that the failure in the reagent or the standard solution is attributable to the adverse affection on the measurement results of the patient specimen, the reagent or the standard solution which has been used for each of the patient specimens has to be confirmed one by one so as to identify the patient specimen for which the reagents or the calibration curve data of the standard solution have been used even if it may not lead to the data failure. This has required a lot of labor and time.

In order to confirm and verify reliability of the analysis results, each distribution of measurement results of not only the reagent but also the standard solution, the accuracy control sample, and the specimen has to be confirmed, thus making the above-described work troublesome and time-consuming.

It is an object of the present invention to actualize the automatic analyzer which allows quick and easy identification of the patient specimen for which the specific reagent or standard solution has been used, and further easy confirmation and verification of reliability of the analysis results.

Solution to Problem

In order to achieve the above-described object, the present invention is configured as described below.

The automatic analyzer includes an analysis system for analyzing a specimen using a reagent, a standard solution, and an accuracy control sample, a storage unit for storing results of using the reagent, the standard solution, and the accuracy control sample in the analysis system, and an analysis result of the specimen, a display unit, an operation input unit for inputting an operator's instruction, and a display control unit for displaying a reagent use time area in which the reagent is selected in accordance with the instruction from the operation input unit among the reagent, the standard solution, the accuracy control sample, and the analysis result of the specimen, which have been stored in the storage unit, and displaying the analysis result of the specimen which has been analyzed using the reagent, the standard solution, and the accuracy control sample in the reagent use time area.

Advantageous Effects of Invention

The present invention is capable of actualizing the automatic analyzer which allows quick and easy identification of the patient specimen for which the specific reagent or standard solution has been used, and further easy confirmation and verification of reliability of the analysis results.

DESCRIPTION OF EMBODIMENT

An embodiment according to the present invention will be described referring to the attached drawings.

EMBODIMENT

Figure 2:
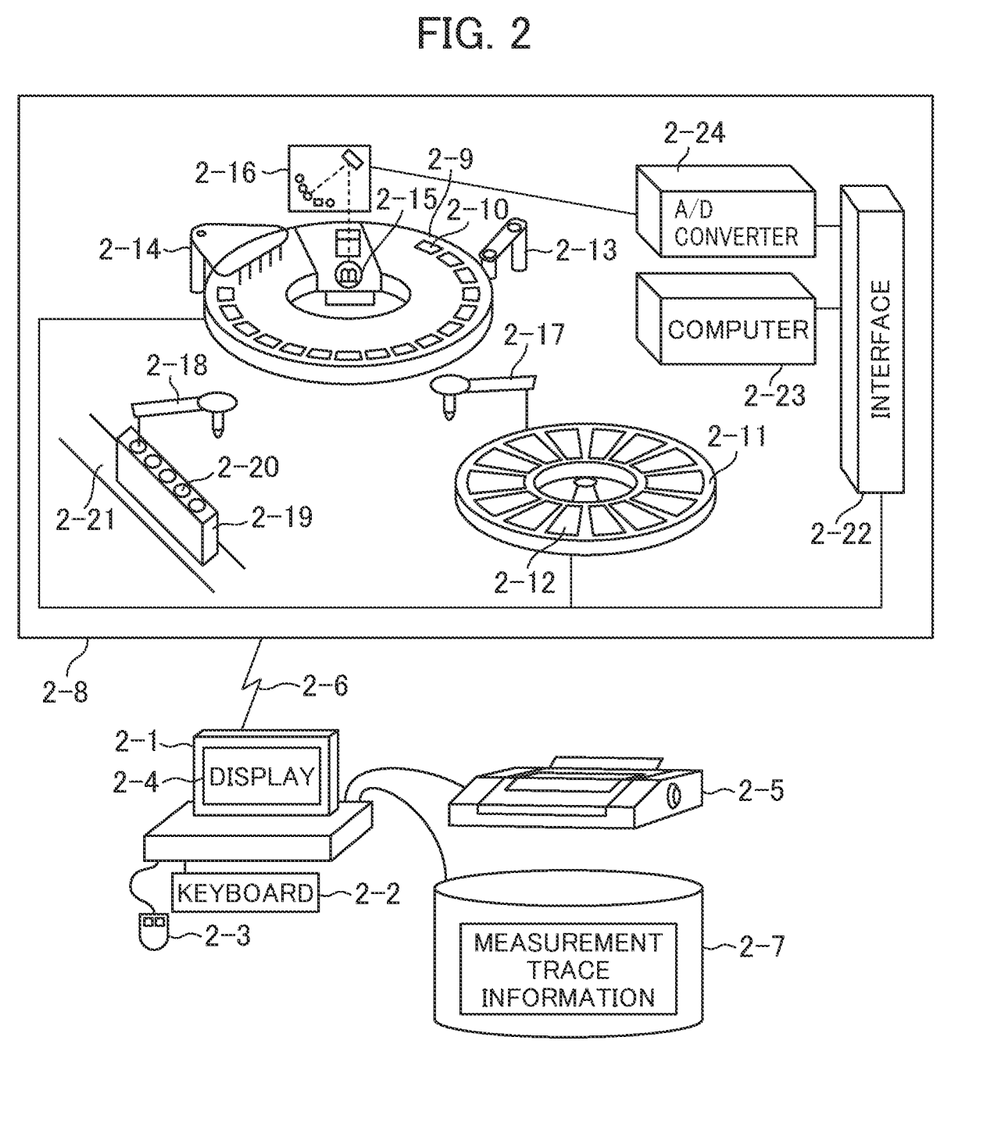
FIG. 2 is a view schematically showing an overall structure of an automatic analyzer in principle, to which the present invention is applied.

FIG. 2 is a view schematically showing an overall structure of an automatic analyzer in principle, to which the present invention is applied.

Referring to FIG. 2, a code 2-1 as an operation unit (also serving as a display control unit) denotes a computer which includes peripheral devices such as a keyboard 2-2 and a mouse 2-3 for data inputting, a display 2-4 for data display, a printer 2-5 for data printing, an interface 2-6 for connection to an analysis system, and a storage unit 2-7 for storing measurement trace information and the like.

A code 2-8 denotes an analysis system connected to the operation unit 2-1 via the interface 2-6. A code 2-9 of the analysis system 2-8 denotes a reaction disk, having a plurality of reaction vessels 2-10 concentrically disposed. A code 2-11 denotes a reagent disk, having a plurality of reagent bottles 2-12 filled with the respective reagents concentrically disposed. A stirring device 2-13, a cleaner 2-14, a light source 2-15, a multi-wavelength photometer 2-16 are disposed around the reaction disk 2-9.

A reagent dispensing probe 2-17 is disposed between the reaction disk 2-9 and the reagent disk 2-11. A rack 2-19 moves on a rack carrier belt 2-21. A plurality of sample vessels 2-20 each filled with the sample are disposed in the rack 2-19. A sample dispensing probe 2-18 is disposed between the reaction disk 2-9 and the rack carrier belt 2-21. All operations of the above-described mechanisms are controlled by a computer 2-23 via an interface 2-22.

An operator requests the measurement item using the display 2-4, the keyboard 2-2, or the mouse 2-3 of the operation unit 2-1, and gives a measurement instruction to the analysis system 2-8. The measurement instruction is transmitted to the analysis system 2-8 via the interface 2-6. The analysis system 2-8 executes the measurement operation as described below in accordance with the received measurement instruction.

The sample dispensing probe 2-18 dispenses the given amount of the sample contained in each of the sample vessels 2-20 into the reaction vessels 2-10 by the number corresponding to the requested items. Upon completion of dispensation to one of the sample vessels 2-20, the rack carrier belt 2-21 moves the rack 2-19 so that the next sample vessel 2-20 is positioned just below the sample dispensing probe 2-18. The reaction disk 2-9 rotates to allow movement of the sample-dispensed reaction vessel 2-10 on the reaction disk 2-9 while rotating.

During the operation as described above, the sample in the reaction vessel 2-10 is subjected to the process executed by the reagent dispensing probe 2-17 for dispensing the reagent in the reagent bottle 2-12, the process executed by the stirring device 2-13 for stirring the reaction liquid, and the process executed by the light source 2-15 and the multi-wavelength photometer 2-16 for measuring absorbance. The reaction vessel 2-10 having the measurement finished is then washed by the cleaner 2-14.

The measured absorbance signal is supplied to the computer 2-23 by way of an A/D converter 2-24 via the interface 2-22. In reference to the absorbance signal, calibration curve data are calculated from the set density data for the standard solution based on the analysis process preliminarily set for each measurement item. For the patient specimen and the accuracy control sample, the density data are calculated from the calibration curve data derived from measurement of the standard solution.

The information of ID/code, lot, expiration date, measurement date is added to those data to provide the measurement results, which will be transmitted to the operation unit 2-1 via the interface 2-6. They are stored in the storage unit 2-7, and printed by the printer 2-5.

Using the display 2-4, the keyboard 2-2, and the mouse 2-3, the automatic analyzer executes the above-described operations for identifying the patient specimen which is suspected to be misdiagnosed owing to the reagent or the standard solution.

Figure 1:
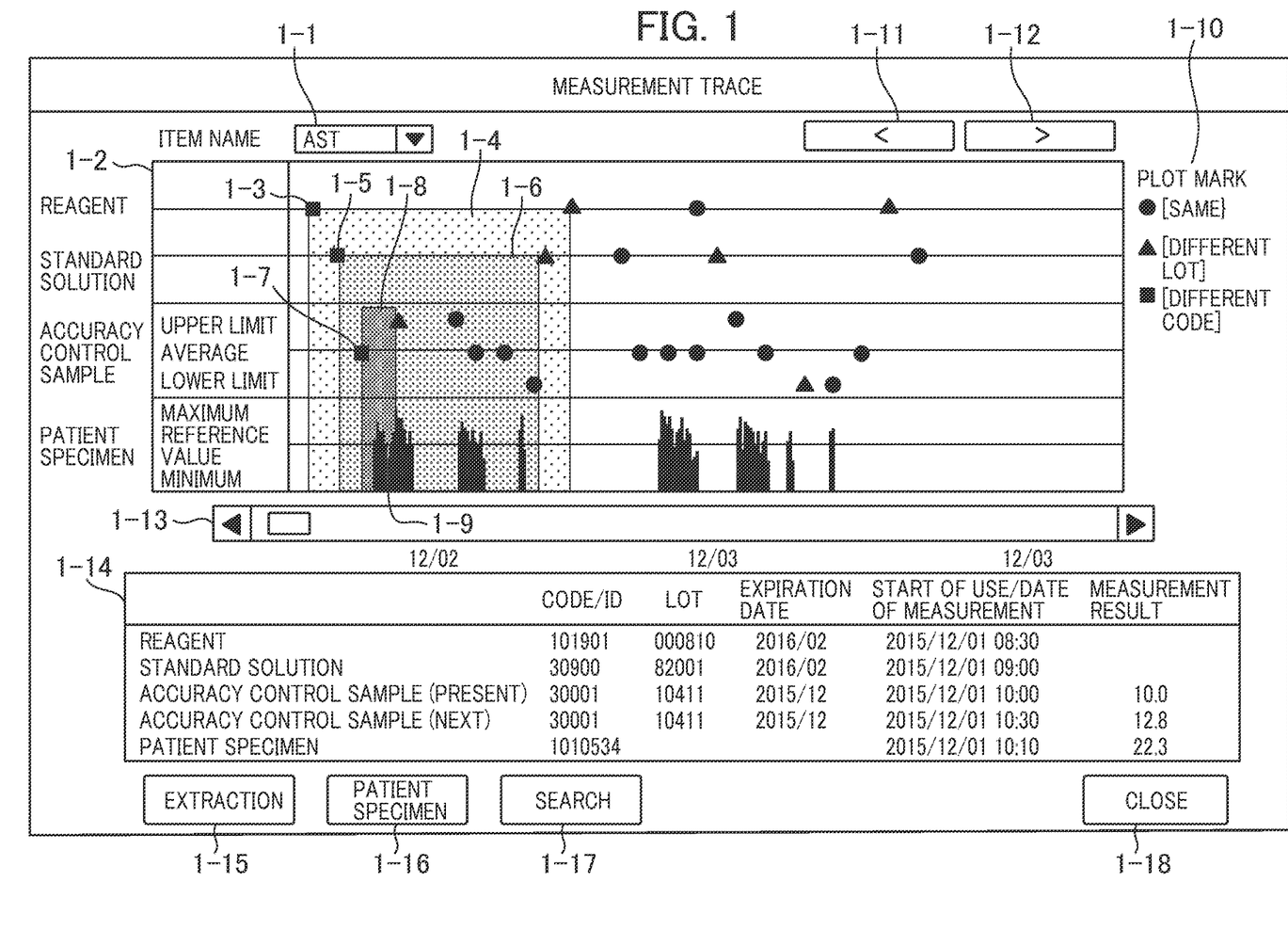
FIG. 1 is a view showing a measurement trace screen according to an embodiment of the present invention.

FIG. 1 is a view showing a measurement trace screen according to an embodiment of the present invention. The measurement trace screen will be displayed in response to designation on the screen of the display 2-4, replacing the screen that has been displayed before. The measurement trace screen displays a chart indicating a course of operations including start of using the reagent, measurement of the standard solution, measurement of the accuracy control sample, and measurement of the patient specimen with respect to the designated measurement item in a time series manner.

Referring to FIG. 1, when the operator selects the measurement item from an item name combo box 1-1 through the keyboard 2-2 or the mouse 2-3, the measurement state of the selected measurement item is displayed in a chart in a time series manner on a chart display area 1-2 for plotting operations including the start of using the reagent, the measurement of the standard solution, the measurement of the accuracy control sample, and the measurement of the patient specimen.

A plot mark 1-10 to be displayed is determined depending on whether codes and lots each as management information of the reagent, the standard solution, and the accuracy control sample are the same as or different from those used last time. A black round mark as a "same" mark indicates that both the code and the lot are the same. That is, the reagent, the standard solution, the accuracy control sample are the same as those used last time. A black triangle mark as a "different lot" mark indicates that the code is the same, but the lot is different. That is, the reagent, the standard solution, the accuracy control sample are in the lot different from those in the lot used last time. A black square mark as a "different code" mark indicates that the code is different. That is, the reagent, the standard solution, the accuracy control sample are different from those used last time because of the different code.

All plots inside the chart display area 1-2 are selectable with the mouse 2-3, displaying the measurement information of the area where the plot selected by the mouse 2-3 has been measured using the reagent, the standard solution, and the accuracy control sample.

The chart display area 1-2 shown in FIG. 1 displays the area as a result of selecting a plot 1-3 of starting the use of the reagent, a plot 1-5 of measuring the standard solution, a plot 1-7 of measuring the accuracy control sample, or a plot 1-9 of measuring the patient specimen.

The plot 1-3 represents the start of using the reagent. A reagent use area (reagent use time area) 1-4 represents a period from a time point of starting the use of the reagent as indicated by the plot 1-3 until a time point of starting the use of the next reagent. At the end of using the reagent in the reagent use area 1-4, the black triangle mark as the "different lot" mark is displayed. In other words, the reagent use area (reagent use time area) represents the time area up until the reagent bottle is changed.

The standard solution, the accuracy control sample, the patient specimen contained in the reagent use area 1-4 represent that the measurement has been performed using the same reagent. The plot 1-5 represents generation of the calibration curve data from the standard solution. A standard solution use area (standard solution use time area) 1-6 represents a period from a time point of generating the calibration curve data from the standard solution indicated by the plot 1-5 until a time point of generating the calibration curve data from the next standard solution. At the end of using the standard solution use area 1-6, the black triangle mark as the "different lot" mark is displayed. The subsequent black round mark represents that the measurement has been performed using the same accuracy control sample as the one which has been used last time as described above. The mark in the standard solution use area 1-6 includes the value of the measurement result displayed with respect to the y-axis. The large value of the measurement result is plotted at the upper section, and the small value is plotted at the lower section.

The accuracy control sample and the patient specimen contained in the standard solution use area 1-6 represent that the measurement result has been calculated using the calibration curve data from the same standard solution.

A plot 1-7 represents measurement of the accuracy control sample. An accuracy control sample use area (accuracy control sample use time area) 1-8 represents a period from a time point of measuring the accuracy control sample as indicated by the plot 1-7 until a time point of the next measurement. At the end of using in the accuracy control sample use area 1-8, the black triangle mark as the "different lot" mark is displayed.

The patient specimen contained in the accuracy control sample use area 1-8 represents that such patient specimen is included in the same accuracy control. A patient specimen selection mark 1-9 represents the currently selected patient specimen. The measurement performed for one of the patient specimens is plotted with respect to a vertical line. The length of the vertical line represents the size of the measurement result. Taking a reference value as the center, the longest length corresponds to the maximum value, and the shortest length corresponds to the minimum value.

The standard solution use area 1-6, the accuracy control sample use area 1-8, and analysis results of the patient specimen are displayed in the display region of the reagent use area 1-4.

The reagent use area 1-4, the standard solution use area 1-6, and the accuracy control sample use area 1-8 are displayed while being differently highlighted.

The display as described above allows identification of the standard solution, the accuracy control sample, and the patient specimen using the reagent indicated by the plot 1-3 in the reagent use area 1-4. It is also possible to identify the accuracy control sample and the patient specimen using the standard solution as indicated by the plot 1-5 in the standard solution use area 1-6.

It is further possible to identify the patient specimen which has been measured after measuring the accuracy control sample as indicated by the plot 1-7 in the accuracy control sample use area 1-8.

The patient specimen selection mark 1-9 may be moved leftward by depressing a button 1-11, and moved rightward by depressing a button 1-12. The patient specimen selection mark 1-9 is schematically displayed as a graph (bar graph) indicating the analysis result of the patient specimen (displaying the value relative to the maximum value, the average value, the minimum value).

It is possible to change the measurement date of the plot displayed on the chart display area 1-2 through movement with a scroll bar 1-13. Referring to an example shown in FIG. 1, the date is displayed below the scroll bar 1-13.

A measurement information 1-14 is a measurement information display region for displaying the information including a code, a lot, an expiration date, a use start date of the reagent that the operator has started using as indicated by the plot 1-3, a code, a lot, an expiration date, a measurement date of the standard solution for generating the calibration curve data as indicated by the plot 1-5, codes, lots, expiration dates, measurement dates of both the measured accuracy control sample and the next measured accuracy control sample as indicated by the plot 1-7, and an ID, a measurement date, and a measurement result of the patient specimen selected with the patient specimen selection mark 1-9, all of which are expressed in figures. The measurement information 1-14 displays the information of the accuracy control sample and the one subsequently used, the information of the used standard solution, and the information of the reagent with respect to the selected patient specimen (code: 1010534) as a reference. This makes it possible to easily identify the information of the accuracy control sample, the standard solution, and the reagent which may influence the measurement result of the selected patient specimen. If the different patient specimen is selected, the information of the accuracy control sample and the one subsequently used, the information of the used standard solution, and the information of the reagent with respect to the newly selected patient specimen will be updated and displayed. Additionally, the corresponding highlighting display area is also updated and displayed.

Figure 3:
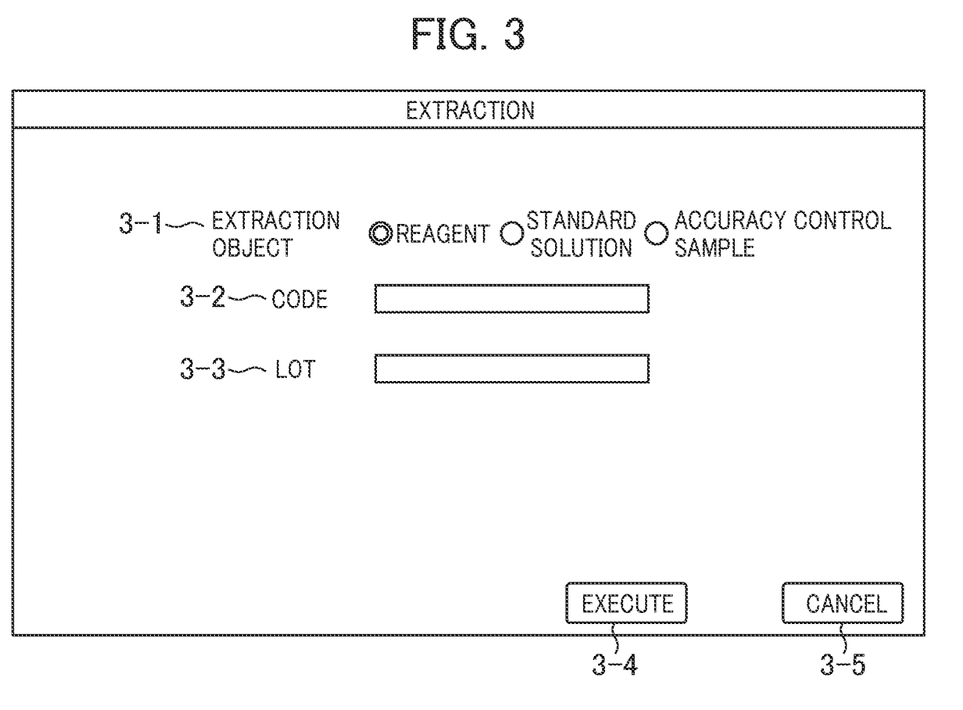
FIG. 3 is a view showing an extraction screen which will be displayed by depressing an extraction button.
Figure 4:
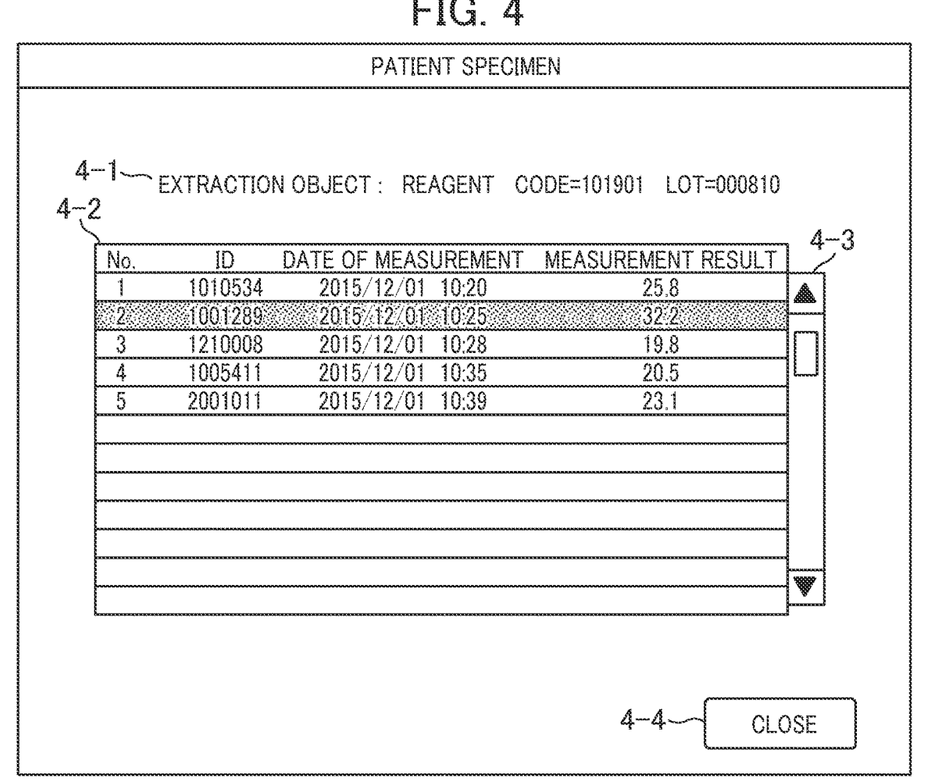
FIG. 4 is a view showing a patient specimen screen which will be displayed by depressing a patient specimen button.
Figure 5:
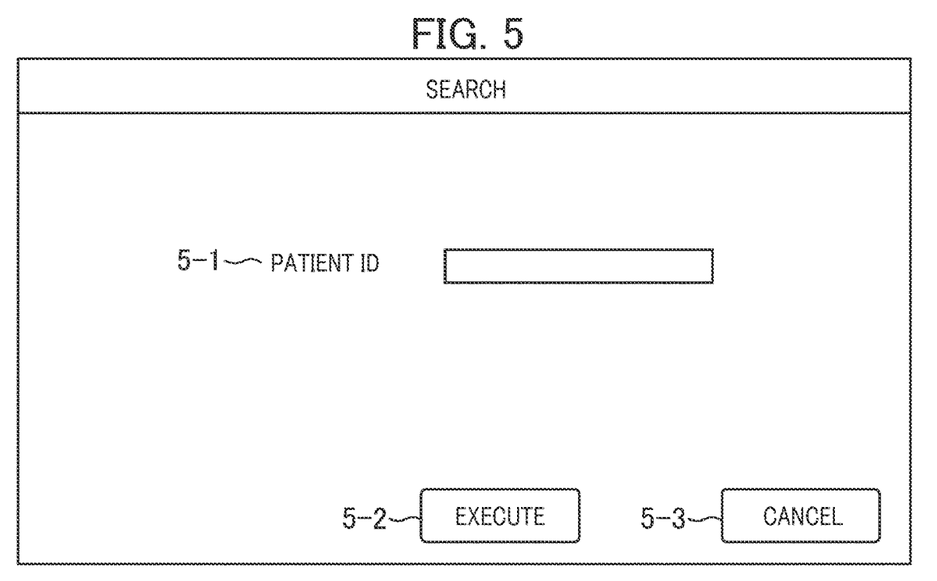
FIG. 5 is a view showing a search screen which will be displayed by depressing a search button.

The extraction screen as shown in FIG. 3 will be displayed by depressing an extraction button 1-15. The patient specimen screen as shown in FIG. 4 will be displayed by depressing a patient specimen button 1-16. The search screen as shown in FIG. 5 will be displayed by depressing a search button 1-17. The measurement trace screen will be closed by depressing a close button 1-18.

FIG. 3 shows the extraction screen to be displayed by depressing the extraction button 1-15 as described above. It is possible to select any one of the reagent, the standard solution, and the accuracy control sample, each as the extracting object with an extracting object radio 3-1 on the extraction screen as shown in FIG. 3.

A code as the management information of the extracting object is input in a code text box 3-2. A lot as the management information of the extracting object is input in a lot text box 3-3. In response to an input of an execution button 3-4, the extraction screen as shown in FIG. 3 will be closed. Then the use area determined on the basis of the plot of either the reagent, the standard solution or the accuracy control sample as the extracting object, which has been input on the extraction screen as shown in FIG. 3 will be displayed on the measurement trace screen as shown in FIG. 1. Furthermore, the use area of the reagent, the standard solution, or the accuracy control sample, either of which has been used for the extracting object, or has used the extracting object will be displayed. The measurement information of the respective plots will be displayed in the measurement information 1-14. It is possible to identify the patient specimen which has been measured using the extracting object in reference to the above-described display.

FIG. 4 shows the patient specimen screen to be displayed by depressing the patient specimen button 1-16 as shown in FIG. 1. Referring to FIG. 4, the extracting object set on the extraction screen as shown in FIG. 3 is displayed in an extracting object 4-1. A patient specimen list 4-2 displays a list of the patient specimens which have been measured using the extracting object. Even if all the patient specimens cannot be displayed at a time, they can be scroll displayed through a scroll bar 4-3. The patient specimen screen will be closed by inputting a close button 4-4.

FIG. 5 shows the search screen to be displayed by depressing the search button 1-17 as shown in FIG. 1. Referring to FIG. 5, an ID of the patient as a searching object is input in a patient ID text box 5-1. The search screen will be closed by inputting an execution button 5-2 so as to display each use area of the reagent, the standard solution, the accuracy control sample which have been used for measuring the patient specimen searched on the measurement trace screen as shown in FIG. 1 while using the selection patient specimen mark 1-9. The measurement information of each plot will be displayed in the measurement information 1-14. It is possible to identify the reagent, the standard solution, the accuracy control sample, which have been used for measuring the patient specimen as the searching object in reference to the above-described display. The search screen will be closed by inputting a cancel button 5-3.

Figure 6:
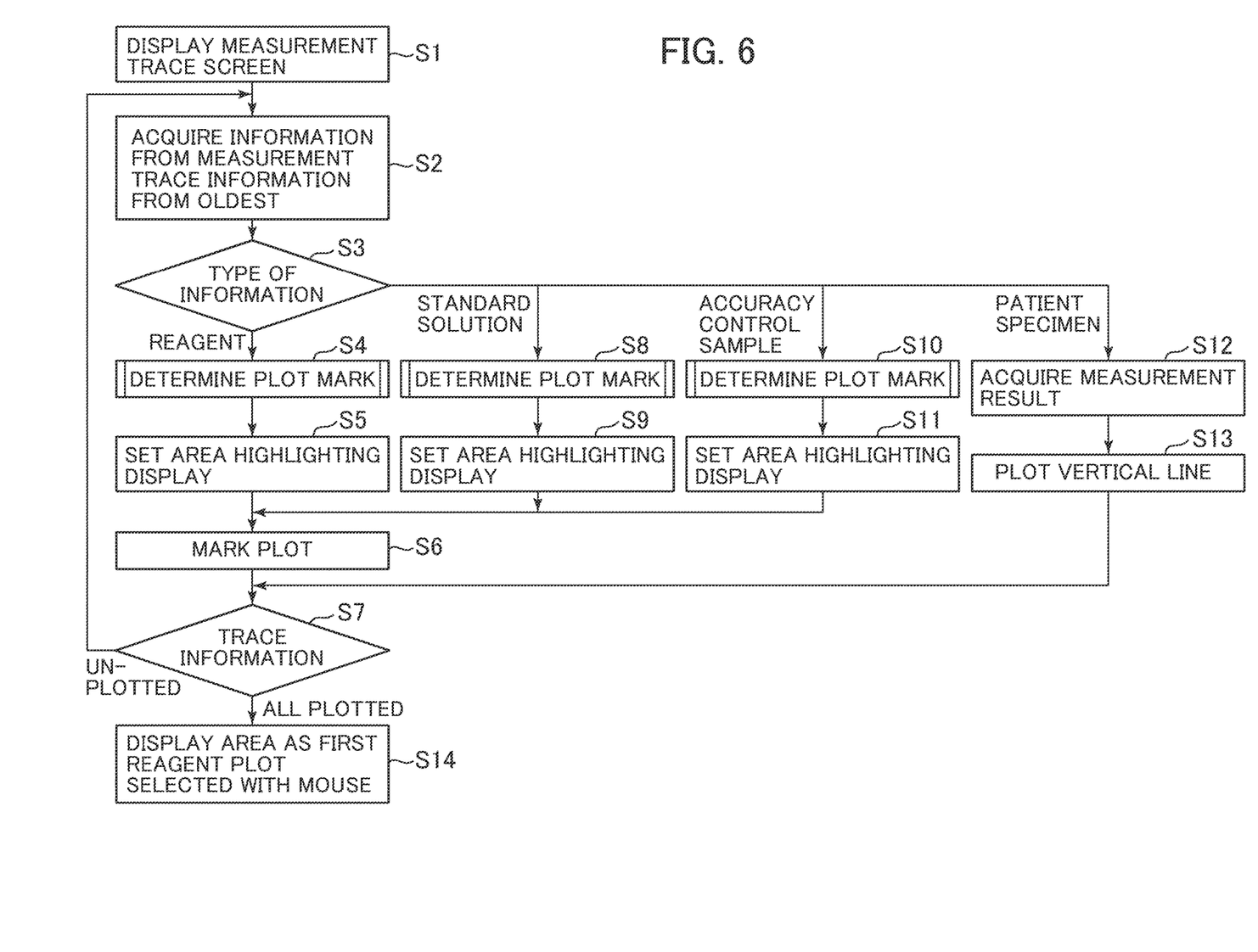
FIG. 6 is a flowchart representing an operation process for displaying the measurement trace screen.

FIG. 6 is a flowchart representing an operation process for displaying the above-described measurement trace screen.

The measurement trace screen is displayed on the display 2-4 in response to an operator's instruction to display the measurement trace screen (step S1). Then the operation unit 2-1 acquires information from the measurement trace information stored in the storage unit 2-7 from the oldest one (step S2). A judgement on the information type is made (step S3).

In step S3, if the information type is judged as the reagent, the above-described plot mark is determined (step S4). The area highlighting display is set (step S5), and the mark is plotted (step S6).

Likewise, in step S3, if the information type is judged as the standard solution or the accuracy control sample, the corresponding plot mark is determined as described above (step S8, S10). The area highlighting display is set (step S9, S11), and the mark is plotted (step S6).

In step S3, if the information type is judged as the patient specimen, the measurement result of the patient is acquired (step S12), and plotted with respect to the vertical line (step S13).

It is judged whether or not the trace information has been all plotted. If unplotted information exists, the process returns to step S2. If the trace information has been all plotted, the area is displayed indicating that the first reagent plot has been selected with the mouse (step S14).

Figure 7:
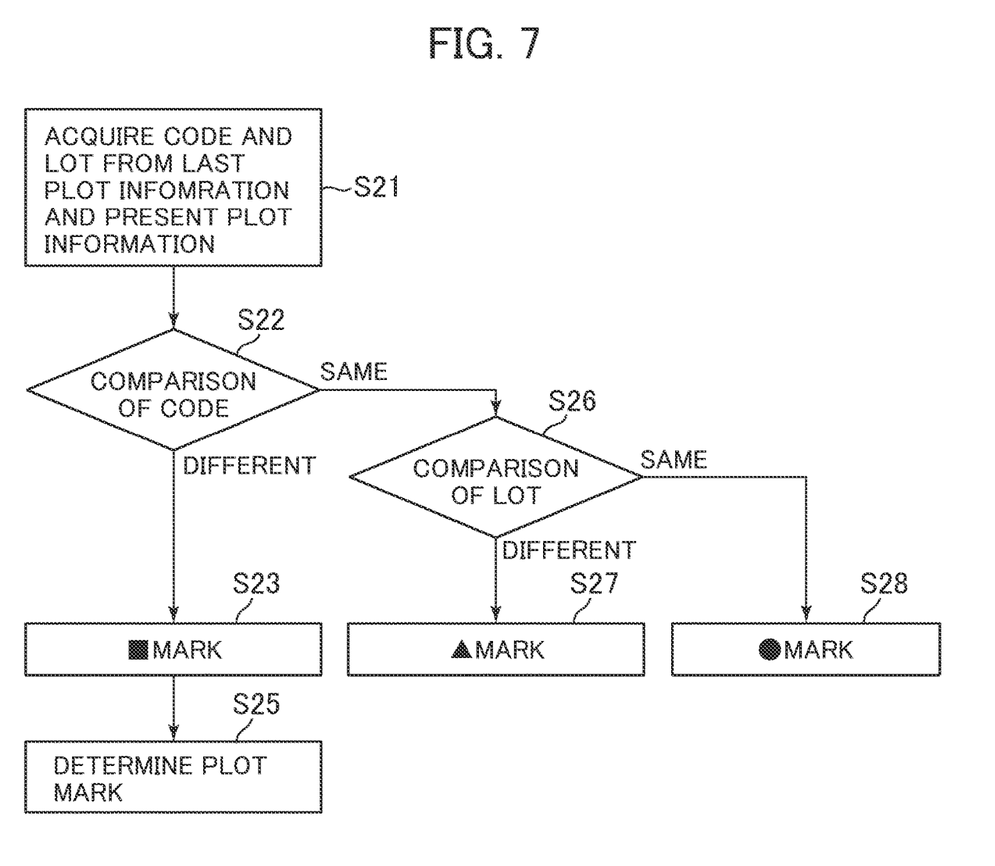
FIG. 7 is a flowchart representing an operation process for determining a plot mark as shown in FIG. 6.

FIG. 7 is a flowchart representing an operation process for determining the plot mark in steps S4, S8, S10 as shown in FIG. 6.

In step S21 as shown in FIG. 7, the information of the code and the lot will be acquired from the plot information displayed last time, and the plot information to be presently displayed.

The last code is compared with the present code (step S22). If those codes are different, the mark is judged as the black square (step S23), and the plot mark is determined accordingly (step S25).

If the last code and the present code are different in step S22, the last lot is compared with the present lot (step S26). If those lots are different, the mark is judged as the black triangle (step S27), and the plot mark is determined accordingly (step S25).

If the last lot and the present lot are the same in step S26, the mark is judged as the black round (step S28), and the plot mark is determined accordingly (step S25).

Figure 8:
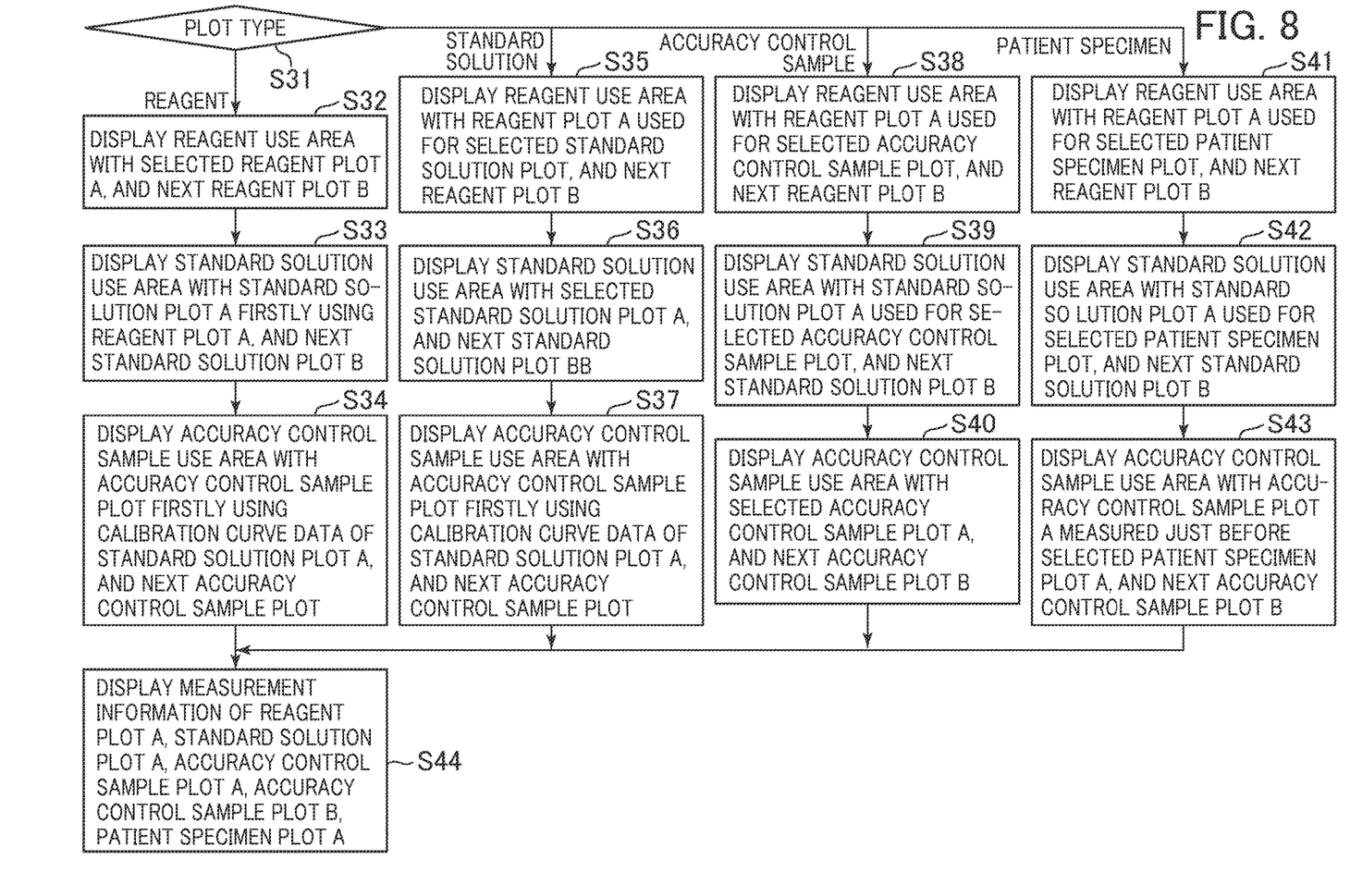
FIG. 8 is a flowchart representing an operation process for displaying measurement information of a plot measurement area where each of the reagent, the standard solution, the accuracy control sample has been used, and measurement information of the patient specimen while using a mouse.

FIG. 8 is a flowchart of an operation process for displaying the measurement information of the area where the above-described plots have been measured using the reagent, the standard solution, the accuracy control sample, and the measurement information of the patient specimen while using the mouse 2-3.

In step S31 as shown in FIG. 8, the plot type (reagent, standard solution, accuracy control sample, patient specimen) is selected. If the selected plot type is the reagent, the reagent use area is displayed with the selected reagent plot A, and the next reagent plot B (step S32). The standard solution use area is displayed with the standard solution plot A firstly using the reagent plot A, and the next standard solution plot B (step S33).

Then the accuracy control sample use area is displayed with the accuracy control sample plot firstly using the calibration curve data of the standard solution plot A, and the next accuracy control sample plot (step S34).

The measurement information of the reagent plot A is displayed in the measurement information 1-14 (step S44). The measurement information 1-14 displays the previous information which will be changed by performing the above-described operation with the mouse 2-3 (which applies not only to the reagent but also the standard solution, the accuracy control sample, the patient specimen).

If the selected plot type is the standard solution, the reagent use area is displayed with the reagent plot A used for the selected standard solution plot, and the next reagent plot B (step S35). Then the standard solution use area is displayed with the selected standard solution plot A, and the next standard solution plot B (step S36).

The accuracy control sample use area is displayed with the accuracy control sample plot firstly using the calibration curve data of the standard solution plot A, and the next accuracy control sample plot (step S37). The measurement information of the standard solution plot A is displayed in the measurement information 1-14 (step S44).

If the selected plot type is the accuracy control sample, the reagent use area is displayed with the reagent plot A used for the selected accuracy control sample plot, and the next reagent plot B (step S38). The standard solution use area is displayed with the standard solution plot A used for the selected accuracy control sample plot, and the next standard solution plot B (step S39).

The accuracy control sample use area is displayed with the selected accuracy control sample plot A, and the next accuracy control sample plot B (step S40). The measurement information of the accuracy control samples A and B is displayed in the measurement information 1-14 (step S44).

If the selected plot type is the patient specimen, the reagent use area is displayed with the reagent plot A used for the selected patient specimen plot, and the next reagent plot B (step S41). The standard solution use area is displayed with the standard solution plot A used for the selected patient specimen plot, and the next standard solution plot B (step S42).

Then the accuracy control sample use area is displayed with the accuracy control sample plot A measured just before the selected patient specimen plot A, and the next accuracy control sample plot B (step S43). The measurement information of the specimen patient A is displayed in the measurement information 1-14 (step S44).

Figure 9:
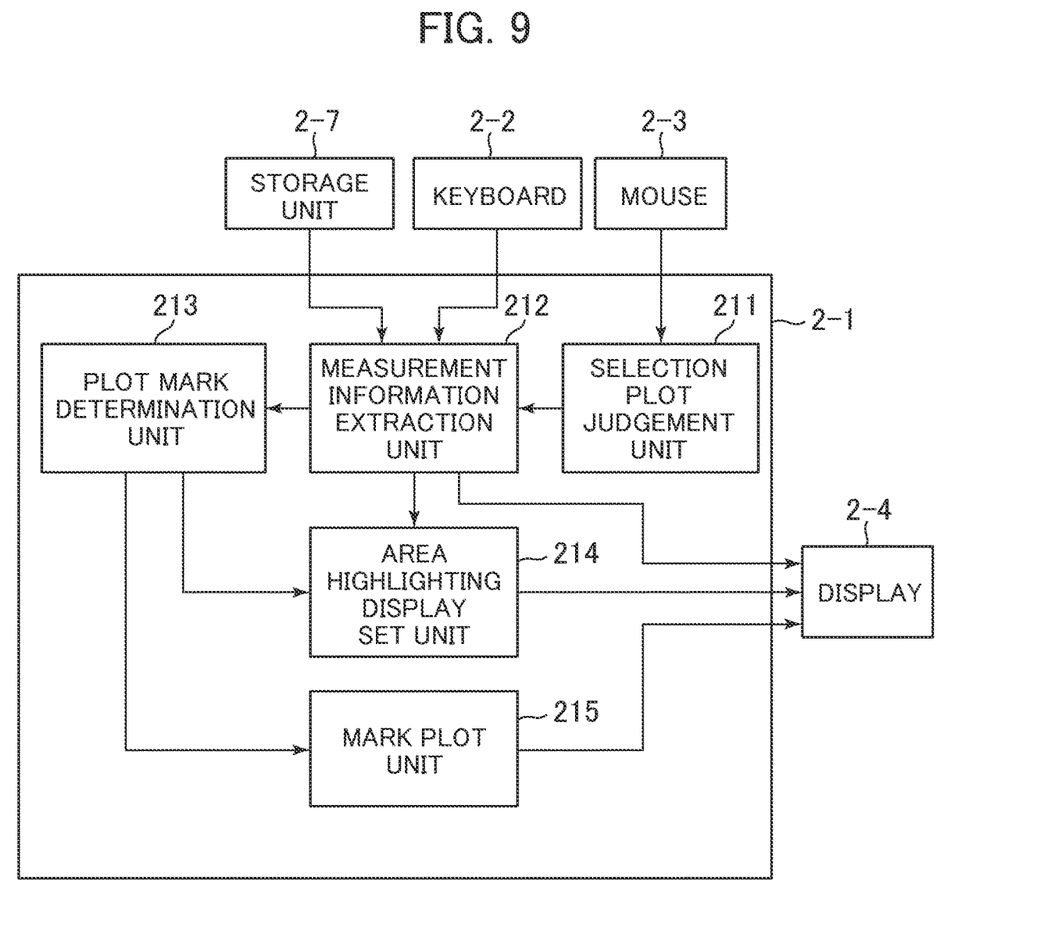
FIG. 9 is a function block diagram with respect to a display control executed by an operation unit (display control unit).

FIG. 9 is a function block diagram indicating a display control operation executed by the operation unit (display control unit) 2-1 for executing operations as described referring to FIGS. 6, 7, 8.

Referring to FIG. 9, the operation unit 2-1 includes a selection plot 211, a measurement information extraction unit 212, a plot mark determination unit 213, an area highlighting display set unit 214, and a mark plot unit 215.

The selection plot judgement unit 211 identifies the selected plot in accordance with the instruction from the mouse 2-3, and supplies the judgement result to the measurement information extraction unit 212. The measurement information extraction unit 212 extracts the measurement information from the storage unit 2-7 in accordance with the information from the keyboard 2-2 or the selection plot judgement unit 211, and supplies the extracted information to the plot mark determination unit 213, and the area highlighting display set unit 214. The measurement information extraction unit 212 supplies the extracted information to the display unit 2-4. The display unit 2-4 displays the measurement information 1-14 in accordance with the information from the measurement information extraction unit 212.

The plot mark determination unit 213 determines the specific plot mark to be set in accordance with the measurement information from the measurement information extraction unit 213, and supplies the determined plot mark to the area highlighting display set unit 214, and the mark plot unit 215.

The area highlighting display set unit 214 sets each highlighting display of the reagent use area 1-4, the standard solution use area 1-6, and the accuracy control sample use area 1-8 based on the information received from the measurement information extraction unit 212 and the plot mark determination unit 213 so as to control the display to be highlighted on the display unit 2-4.

The mark plot unit 215 plots the mark on the screen of the display unit 2-4 based on the information from the plot mark determination unit 213.

As described above, the embodiment of the present invention visually displays the start and the end of using the reagent, the standard solution, and the accuracy control sample by graphics on the same screen while displaying whether the lot/code is the same. Furthermore, the start and the end of measuring the patient specimen are visually displayed by graphics as well as the measurement values on the same screen. The graphically displayed measurement information of the reagent, the standard solution, the accuracy control sample, and the patient specimen will be expressed in figures.

If it is found out that the reagent and the standard solution are attributable to the failure of the measurement result, it is possible to quickly and easily identify the patient specimen subjected to the measurement using the above-described reagent and the standard solution. In the case of abnormality in the accuracy control sample, it is possible to quickly and easily identify the patient specimen subjected to the measurement after measuring the accuracy control sample.

The embodiment according to the present invention actualizes the automatic analyzer capable of quickly and easily identifying the patient specimen for which the specific reagent or the standard solution has been used, and further easily confirming and verifying the reliability of the analysis results.

LIST OF REFERENCE SIGNS 1-1: item name combo box,
1-2: chart display area,
1-3: reagent start of use plot,
1-4: reagent use area,
1-5: standard solution measurement plot,
1-6: standard solution use area,
1-7: accuracy control sample measurement plot,
1-8: accuracy control sample use area,
1-9: patient specimen selection mark,
1-14: measurement information,
2-1: operation unit,
2-2: keyboard,
2-3: mouse,
2-4: display,
2-5: printer,
2-6: interface,
2-7: storage unit,
2-8: analysis system

The invention claimed is:

1. An automatic analyzer comprising:
an analysis system analyzing a specimen using a reagent, a standard solution, and an accuracy control sample;
a storage unit storing results of using the reagent, the standard solution, and the accuracy control sample in the analysis system, and an analysis result of the specimen;
a display unit; and
a computer coupled to the analysis system, the storage unit and the display unit, the computer programmed to:
receive a selection of the reagent among the reagent, the standard solution, the accuracy control sample, and the analysis result of the specimen,
display in a chart display area of a screen a time series of data including a reagent use time area having a first boundary at a first time of using the reagent and a second boundary at a second time of using a subsequent reagent, the second time being subsequent to the first time and the reagent use time area indicating an area of use of the reagent in the time series of data, and
simultaneously display on the chart display area the analysis result of the specimen within the reagent use time area, which has been analyzed using the reagent, the standard solution, and the accuracy control sample.

2. The automatic analyzer according to claim 1,
wherein the computer is programmed to:
simultaneously display a standard solution use time area of the standard solution and an accuracy control sample use time area of the accuracy control sample within the first boundary of the first time and within the second boundary at the second time of the reagent use time area, and
highlight each of the reagent use time area, the standard solution use time area, and the accuracy control sample use time area, differently.

3. The automatic analyzer according to claim 2,
wherein the computer is programmed to display the standard solution use time area of the used standard solution within the reagent use time area, and the accuracy control sample use time area of the accuracy control sample within the standard solution use time area.

4. The automatic analyzer according to claim 3,
wherein the computer is programmed to display a a plurality of predetermined marks for each of the reagent use time area, the standard solution use time area, and the accuracy control sample use time area, which indicate whether respective codes and lots of the reagent and the subsequent reagent are the same, whether respective codes and lots of the standard solution a subsequent standard solution are the same, and whether respective codes and lots of the accuracy control sample and a subsequent accuracy control sample are the same.

5. The automatic analyzer according to claim 4, wherein the computer is programmed to simultaneously display on the screen a measurement information display area for displaying:

the code, the lot, an expiration date, and a use start date of the reagent, the code, the lot, an expiration date, and a measurement date of the standard solution, respective codes, lots, expiration dates, and measurement dates of the accuracy control sample and a next measured accuracy control sample, and an identification (ID), measurement date, and a measurement result of the specimen.

6. The automatic analyzer according to claim 4, wherein the predetermined marks include a first type, a second type and a third type, and wherein the computer is programmed to:

determine whether the subsequent reagent has at least one of a different code and a different lot than the reagent, and display one of the first type, the second type and the third type of the predetermined marks at the first boundary of the first time of the reagent use time area and display one of the first type, the second type and the third type of the predetermined marks at the second boundary of the second time of the reagent use time area, based on whether the subsequent reagent has at least one of the different code and the different lot than the reagent.

7. The automatic analyzer according to claim 1, wherein the first reagent and the subsequent reagent are the same reagent.

* * * * *